United States Patent [19]

Baron

[11] 4,393,867
[45] * Jul. 19, 1983

[54] ANATOMICAL COMPRESSION DEVICE

[76] Inventor: Howard C. Baron, New York, N.Y.

[ * ] Notice: The portion of the term of this patent subsequent to Nov. 17, 1998, has been disclaimed.

[21] Appl. No.: 307,313

[22] Filed: Sep. 30, 1981

Related U.S. Application Data

[63] Continuation-in-part of Ser. No. 104,187, Dec. 17, 1979, Pat. No. 4,300,542.

[51] Int. Cl.$^3$ ............................................. A61F 5/04
[52] U.S. Cl. ............................ 128/87 R; 128/89 R
[58] Field of Search ................. 128/87 R, 89 R, 90, 128/DIG. 20, 165, 166

[56] References Cited

U.S. PATENT DOCUMENTS

| | | | |
|---|---|---|---|
| 3,548,819 | 12/1970 | Davis et al. | 128/87 R |
| 3,662,057 | 5/1972 | Webster et al. | 128/89 R X |
| 4,300,542 | 11/1981 | Baron | 128/87 R |

Primary Examiner—John D. Yasko
Attorney, Agent, or Firm—Schuyler, Banner, Birch, McKie & Beckett

[57] ABSTRACT

An anatomical compression device including a flexible, expandable envelope which contains a pair of chemical agents which form a gas when mixed. In use, the envelope encircles a body part, such as an injured limb, and the chemical agents are mixed by manual manipulation of the envelope, creating a gas which expands the envelope and exerts a compressive force on the limb. The compression device can serve as a splint for broken bones, as a pressure dressing for the control of bleeding, or as a treatment device for minimizing the effect of snake venom or a snake bite victim.

21 Claims, 11 Drawing Figures

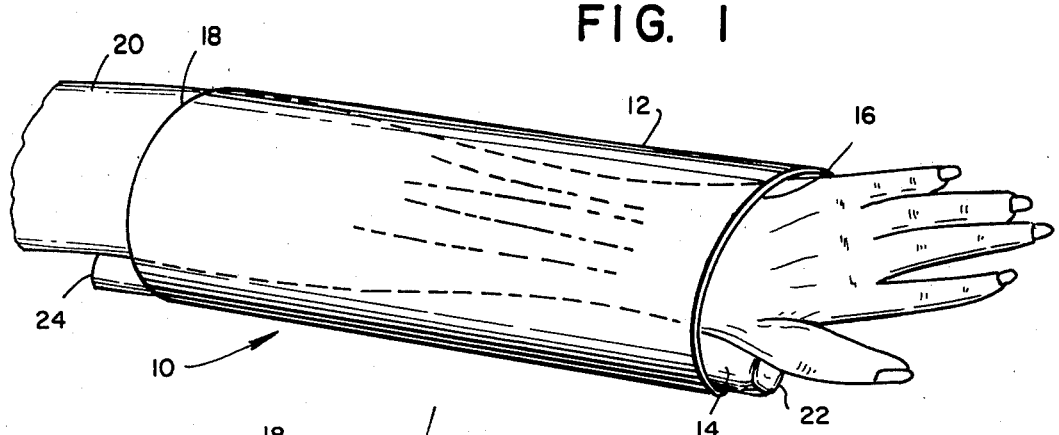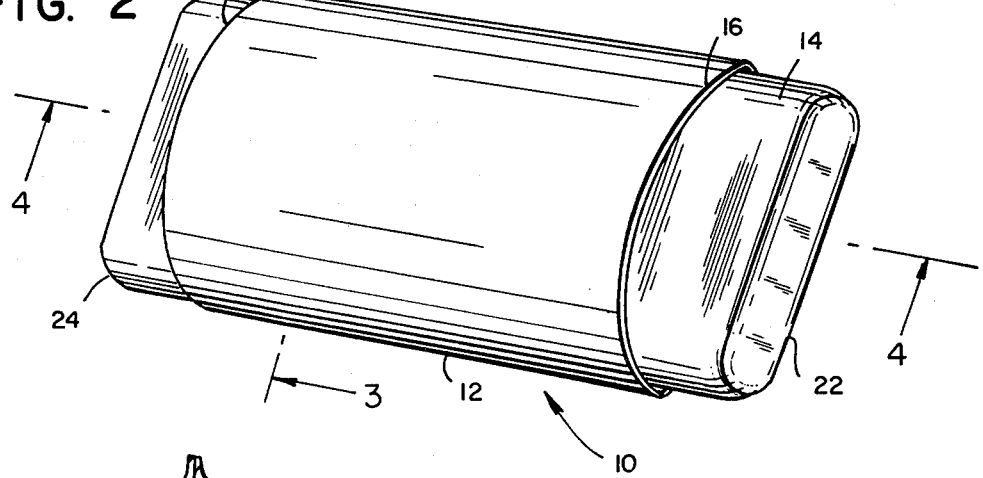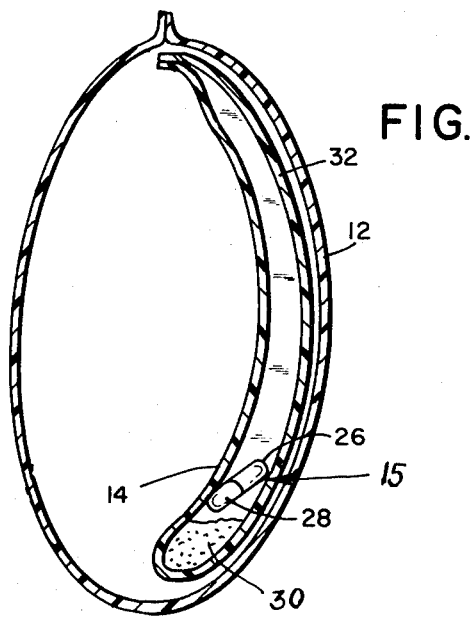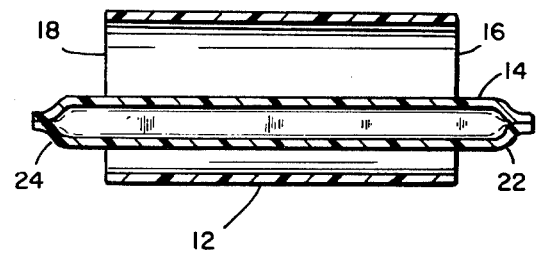

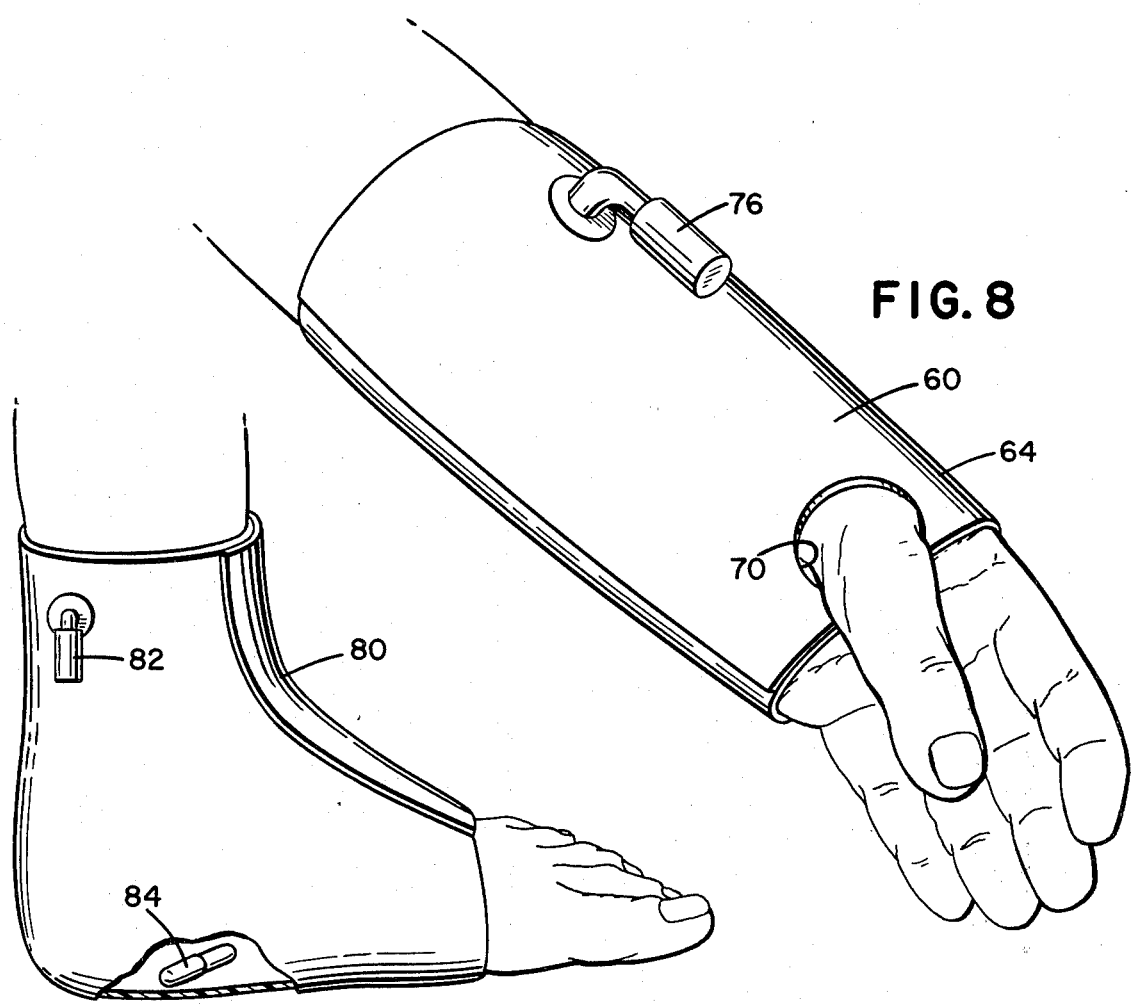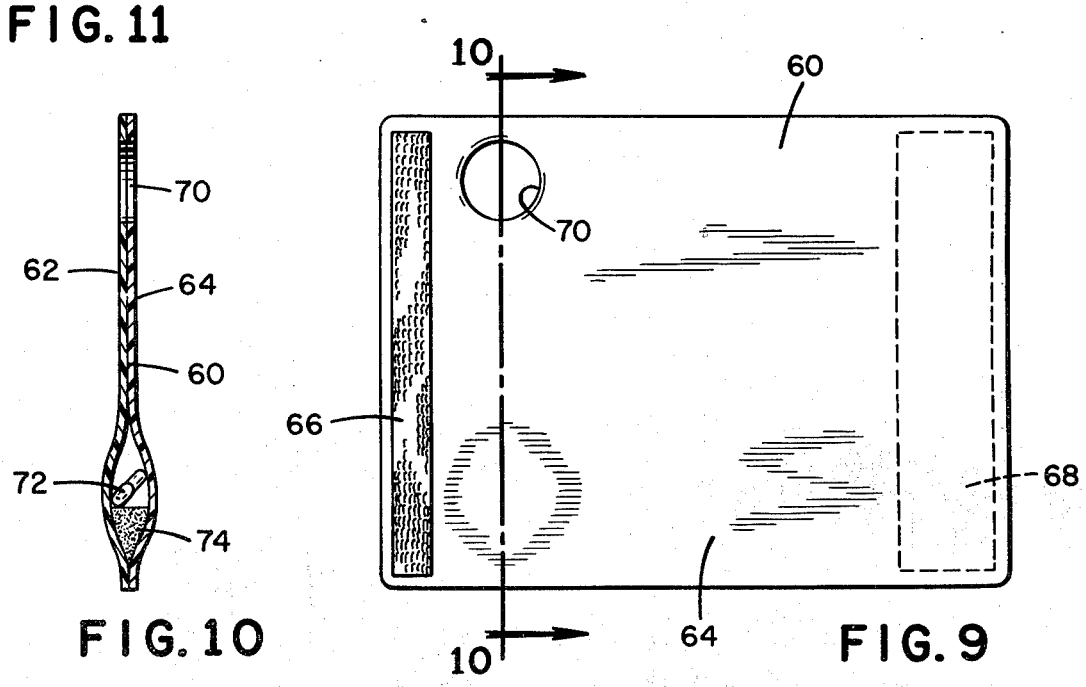

ANATOMICAL COMPRESSION DEVICE

This application is a continuation-in-part of copending application Ser. No. 104,187, filed Dec. 17, 1979 now U.S. Pat. No. 4,300,542.

BACKGROUND OF THE INVENTION

1. Field of the Invention

This invention relates generally to anatomical compression devices and, more particularly, to a compression device adapted to encircle and apply a compressive force to a body part to thereby immobilize it and/or control blood flow.

2. Description of the Prior Art

In the emergency treatment of traumatic injuries to human extremities, there has been a long felt need for a device which can be quickly and easily applied, preferably by the injured person himself, to stabilize the fractured limb and/or to control bleeding.

With the current increased interest and participation in outdoor activities such as hiking, camping, mountain climbing and skiing, an increased number of persons engage in strenuous physical activity, under hazardous or semi-hazardous conditions, often in remote areas and often alone. In such activities it is not uncommon for a participant to sustain severe injuries to a limb. In the case of broken bones it is important to stabilize the limb, provide uniform support, and prevent movement until definitive medical attention can be obtained. Failure to do so often results in aggravating the injury. In extreme cases the broken ends of the bones may even puncture the skin causing the fracture to become compound. The conventional first air procedures require that a splint be obtained or fabricated from materials at hand and that the limb be immobilized by binding it to the splint. This procedure is often difficult to accomplish in remote areas due to the lack of suitable materials. Even if suitable materials are at hand, it is often impossible for an injured person, who is alone, to apply a splint due to the traumatic effects of his injury.

In the case of massive bleeding resulting from a cut or a laceration on a limb, the conventional first aid procedures require that the bleeding be controlled by application of direct pressure on the wound or, if the bleeding cannot be controlled by direct pressure, a tourniquet is applied to control the flow of blood to the limb. Both of these procedures have serious practical limitations. The self-application of a tourniquet is often difficult for an injured person to accomplish due to lack of suitable materials for construction of the tourniquet and the awkwardness and incapacity which results from the trauma of the injury. The application of direct pressure on the wound is usually difficult and sometimes impossible for an injured person to accomplish due to such factors as the awkward location of the wound or the inability to exert sufficient pressure to control the bleeding.

Splinting devices exist which are easier to apply than conventional plaster casts. Some of these are flexible envelopes which are wrapped around the injured limb and are pressurized by an external source, such as a refrigerant supply, an air pump, or even lung power. External pressure sources, however, are usually heavy and cumbersome. In the case of a lone injured individual, it may not be possible for his mouth to reach the inflation mechanism because of the location of the injury, or the trauma of the injury may render him too weak to inflate the device. Often splinting devices comprise a sleeve containing reactive components which, when mixed, form a hardenable mass. In use, the sleeve is manipulated to break the component-containing capsules and mix them so that the chemical reaction can begin. The sleeve is then drawn onto the injured limb, but the limb must be immobilized by some other means until the splint hardens, usually in 5 to 30 minutes. In emergency situations this delay may be intolerable.

SUMMARY OF THE INVENTION

It is a major object of the present invention to provide an anatomical compression device which can be easily applied, even by an injured person, to rapidly stabilize a fractured limb and/or to control bleeding.

Another object of the present invention is to provide an anatomical compression device which can be operated by just one hand.

Another object of the present invention is to provide an anatomical compression device which is extremely light in weight and low in bulk, making it suitable for inclusion in portable first aid kits and for other applications where weight and space are at a premium.

Another object of the invention is the provision of an anatomical compression device which is quickly and easily applied, yet is extremely effective in splinting fractured limbs as well as controlling severe bleeding. The compression device is particularly useful in mass disaster situations where a limited number of medical personnel is available for treating large numbers of injured persons.

Another object of the invention is to provide an anatomical compression device which may be manufactured of clear plastic, thus making the injured area visually accessible.

Still another object of the invention is to provide an anatomical compression device which comprises relatively few parts and which can be easily manufactured using mass production techniques, resulting in a relatively low unit cost.

In accordance with the present invention, the compression device is adapted to encircle and apply a compressive force to an anatomical body part, and comprises a completely sealed, flexible walled, expandable envelope having a central space adapted to receive the body part with the envelope encircling the body part, and inflating means including a frangible member within the envelope for rapidly generating a supply of substantially only gas therein. The frangible member is accessible from the exterior of the envelope through its flexible walls. Thus, the frangible member may be manually ruptured to rapidly generate gas within the envelope, thereby causing the envelope to expand rapidly without further manipulation and apply a compressive force to the body part.

The invention also includes an anatomical compression device adapted to encircle and apply a compressive force to an anatomical body part, comprising a completely sealed, flexible walled, expandable envelope adapted to at least partially encircle the body part, securing means for securing the envelope in an encircling relationship around the body part, and inflating means including a frangible member within the envelope for rapidly generating a supply of substantially only gas therein. The frangible member is accessible from the exterior of the envelope through its flexible walls. Thus, the frangible member may be manually ruptured to rapidly generate gas within the envelope, thereby causing the envelope to expand rapidly without further manipulation and apply a compressive force to the body part.

BRIEF DESCRIPTION OF THE DRAWINGS

Additional objects and advantages of the present invention will become apparent from the following detailed description of the invention when taken in connection with the accompanying drawings, in which:

FIG. 1 is a perspective view of an anatomical compression device made in accordance with the present invention, shown in use stabilizing a fracture of the radius and the ulna bones which are shown in broken lines on a fragmentary drawing of a forearm;

FIG. 2 is a perspective view of the compression device of FIG. 1 showing only the compression device and not the forearm;

FIG. 3 is a cross-sectional view taken along line 3—3 of FIG. 2, showing the expandible envelope in a flattened state;

FIG. 4 is a cross-sectional view taken along line 4—4 of FIG. 3, showing the expandible envelope inflated;

FIG. 8 is a perspective view of a modified form of compression device according to the invention shown in use on the forearm and wrist of a patient;

FIG. 9 is a plan view of the compression device of FIG. 8 shown in a flattened state prior to application to the forearm and wrist;

FIG. 10 is a cross-sectional view of the same taken along line 10—10 of FIG. 9; and FIG. 11 is a perspective view of another form of compression device according to the invention shown in use on the ankle and foot of a patient.

DETAILED DESCRIPTION

Figure 5:
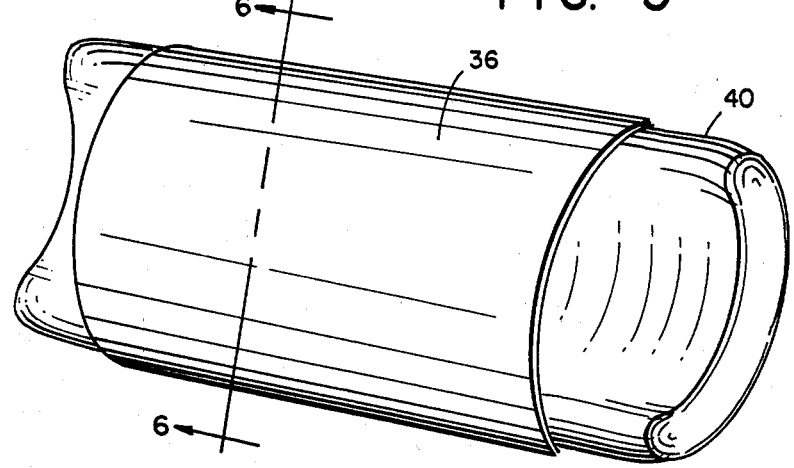
FIG. 5 is a perspective view similar to FIG. 2 showing a modified form of expandible envelope which is curved when inflated.

Referring in detail to the drawings, there is shown in FIGS. 1 to 4, by way of example, a compression device for human limbs 10 in accordance with the present invention, comprising a tubular sleeve member 12, an expandible envelope member 14, and a device 15 for generating gas to inflate the expandible envelope 14. The sleeve member 12 is made of a relatively soft bendable plastic such as transparent polyvinyl chloride, or the like. The sleeve member 12 has open ends 16 and 18 and is of a size so as to permit a human arm 20 or leg to be conveniently inserted therein.

The expandible envelope 14 is preferably made of the same soft and bendable plastic material as the sleeve 12, such as transparent polyvinyl chloride. The expandible envelope 14 is generally elongated in shape and is encircled by the sleeve 12. In the embodiment of the invention shown in FIGS. 1 to 4, the ends 22 and 24 of the envelope 14 project beyond the ends 16 and 18 respectively, of the sleeve 12.

In its initially flattened form, the envelope 14 occupies a minor portion of the sleeve 12 and does not interfere with the sleeve 12 being slipped onto an injured limb.

The gas generation device 15 may consist of a container of compressed gas which may be opened or ruptured to release gas within the envelope or, more preferably it may comprise a store of two or more chemicals which, when mixed, generate gas. The expandible envelope 14, illustrated by way of example, contains at least one thin-walled capsule or ampoule 26 which may be ruptured or crushed to release a chemical agent 28 which then can mix with a chemical agent 30 which is stored within the expandible envelope 14.

Examples of suitable pairs of chemical agents for producing gas when mixed include a measured amount of baking soda in dry powder form stored in the envelope 14 and a supply of water stored in capsule 26. When the capsule 26 is ruptured, the water mixes with baking soda and generates carbon dioxide gas. As another example the capsule 26 may contain a supply of dilute hydrochloric acid and the envelope 14 may contain a supply of calcium carbonate. If the liquid agent is prone to freezing at low ambient temperatures, a small amount of antifreeze agent (such as alcohol) may be included.

Alternatively, the capsule 26 may comprise a thin-walled capsule body having an integral transverse partition wall which is also thin and capable of being easily ruptured when the capsule is squeezed and crushed. At one side of the partition wall, the capsule may contain a measured supply of powdered chemical and at the other side of the partition wall the capsule may contain a supply of a liquid which will react with the powdered chemical to generate gas. Again, an antifreeze agent may be included with the liquid chemical agent.

The transparent characteristics of the plastic material of the sleeve 12 and of the envelope 14 enable first aid personnel to easily monitor the condition of the injured limb. The transparency of the envelope 14 also makes it extremely simple for an operator to locate the capsule 26 in order to inflate the envelope 14.

When inflated, the expandible envelope 14 assumes the general shape of a thick rectangular plate as is shown in FIG. 2. The inflation of the envelope 14 makes the envelope relatively rigid and exerts a uniform pressure on a limb shown inserted in sleeve 12 as is shown in FIG. 1. The device 10 conforms to the anatomical configuration of the limb and the limb is held securely between the sleeve 12 and the expanded envelope 14. The end portions 22, 24 of the envelope 14 which extend beyond the sleeve 12 provide additional stability and protection for the injured limb.

Medical personnel may easily remove the device 10 from a limb by merely cutting or puncturing the envelope 16, as with a knife or a scissors. This causes the gas within the envelope 14 to escape to the atmosphere so that the envelope becomes deflated. The sleeve 12 may then be slipped off the limb for reuse with a new envelope, or alternatively, the sleeve may be easily cut away to expose the limb. Alternatively, a pressure release valve (described below in connection with FIGS. 8–11) may be provided for deflating envelope 14.

In FIG. 3 it will be seen that the sleeve 12 and the envelope 14 are each individually formed by heat sealing the marginal edges of the plastic film material. In an alternative construction, which is not shown, the wall 32 of the envelope 14 may be attached to the sleeve 12 using an appropriate techique such as a cement or a mechanical fastener.

Figure 6:
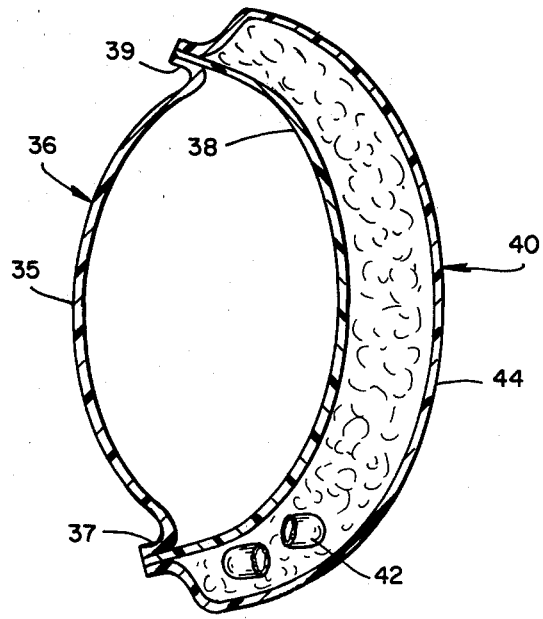
FIG. 6 is a cross-sectional view taken along line 6—6 of FIG. 5.
Figure 7:
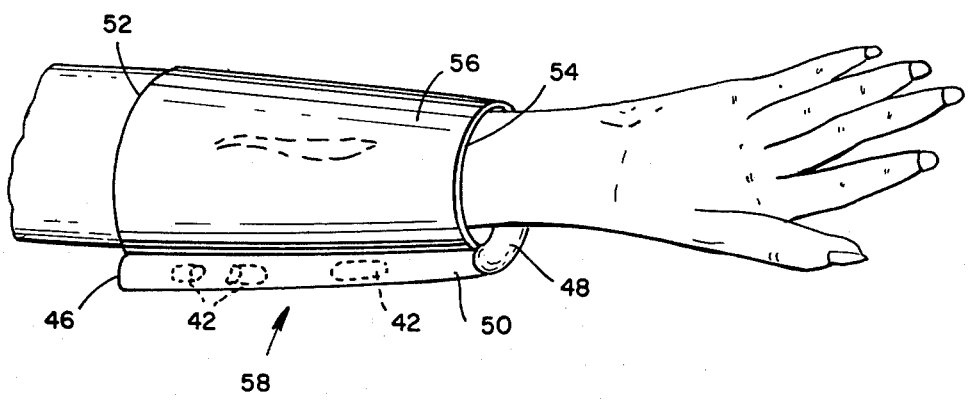
FIG. 7 is a perspective view of another modification of the compression device showing the device in use applying pressure to a wound.

FIGS. 5 to 7 show an alternative construction of the device in which the sleeve member 36 is formed of a single panel 35 of bendable plastic film having edges 37, 39 which are attached by heat sealing to a wall 38 of the expandible envelope 40. Thus the wall 38 serves as both the inner wall of the envelope 40 and the inner wall of the sleeve member 36. Expandible envelope 40 contains a gas generating device comprising a capsule 42 containing a store of liquid chemical and a store of a dry chemical as has been previously described. The panel which forms the outer wall 44 of the expandible envelope 40 is greater in width than the wall 38 so that when inflated, the expandible envelope 40 has the general form of a curved rectangular plate as is shown in FIGS. 5 and 6. This configuration of the expandible envelope 40 provides an additional measure of lateral support and lateral stability for the injured limb.

FIG. 7 shows another alternative construction of the device 50 similar to the construction of FIGS. 5 and 6 except that the ends 46 and 48 of the expandible envelope 50 are generally in line with the ends 52 and 54 of the sleeve 56. The device 58 is shown in use applying pressure to a wound on a forearm 60. The sleeve 56 is transparent so that the wound may be continually inspected. In this alternative construction, the expandible envelope 50 may have a plurality of capsules each containing chemical agents for generating a gas as has been previously described. The pressure exerted on the wound may be increased during operation by rupturing additional capsules and generating additional quantities of gas. The inflation of the expandible envelope 50 creates a uniform pressure exerted on the limb which facilitates controlling the bleeding from the wound.

FIGS. 8 through 10 illustrate another form of compression device according to the invention adapted for application to a forearm and wrist. In this embodiment the expandible envelope 60 has a generally rectangular configuration (FIG. 9) before being applied to the arm and wrist, and is formed of two plastic sheets 62, 64 which are heat sealed together along their marginal edges. The mating components of a separable fabric fastener are secured to sheets 62 and 64 adjacent opposite edges of envelope 60. An example of this type of fastener is that manufactured and sold under the trademark VELCRO, which comprises a strip of pile loops and a mating strip of thermoplastic monofilament hooks adapted to engage the loops of the pile element. In this embodiment, the hooked element 66 is secured to sheet 64, while the pile element 68 is secured to sheet 62. When envelope 60 is wrapped around the forearm and wrist with the opposite edges in overlapping relationship, the hooks of element 66 engage the pile loops of element 68 to secure the envelope in position. Proper comfort and fit are afforded by providing a thumbhole 70 through which the thumb extends. Sheets 62 and 64 are heat sealed together around thumbhole 70 to maintain envelope 60 in a gas tight condition. Envelope 60 contains a gas generating device comprising a capsule 72 containing a store of liquid chemical, and a store of dry chemical 74 as has been previously described. A pressure release valve 76 is provided on the outside of envelope 60. Valve 76 communicates with the interior of the envelope and can be opened either to relieve some of the gas pressure within the envelope or completely deflate the envelope so that it can be removed from the arm.

FIG. 11 illustrates another form of compression device according to the invention adapted for application to an ankle and foot. Envelope 80 is similarly fabricated of two sheets of thermoplastic material. A suitable fastening device (not shown) such as the VELCRO fastener used in the embodiment of FIGS. 8 through 10, is provided adjacent the opposite overlapping edges of envelope 80 to secure the envelope in position around the ankle and foot. A pressure release valve 82 also is provided. Gas generation is accomplished by means of a frangible capsule 84 as previously described.

The compression device of the invention generally may be fabricated to conform to and encircle almost any part of the anatomy. Thus, the compression device may be formed as a knee splint, an elbow splint or even a whole body cast (for spinal fractures, for example) to name just a few. While clear plastic sheets are the preferred material for the compression device, other suitable materials may also be used which are flexible and are gas impervious. Securing devices other than separable fabric fasteners may be used, such as snaps, zippers, buckles, and the like. The compression device may even be formed as a continuous sleeve into which a limb is inserted prior to inflation, thus eliminating the need for securing devices.

With proper regulation of gas pressure the compression device can be used as a snake bite kit to minimize the effect of snake venom on a victim. The pressurized envelope compresses the lymphatics in the soft tissues underneath the skin, and also impedes the return flow of venous blood from the limb, allowing the body to detoxify the venom. However, the pressure exerted is not sufficient to interfere with the arterial supply of blood, so as not to cause any vascular compromise.

While preferred embodiments of the invention have been shown and described herein, it is obvious that numerous omissions, changes and additions will be apparent to those skilled in the art without departing from the spirit and scope of the invention, which is defined by the appended claims.

I claim:

1. An anatomical compression device adapted to encircle and apply a compressive force to an anatomical body part, comprising:
    a completely sealed, flexible walled, expandible envelope adapted to at least partially encircle the body part;
    securing means for securing said envelope in an encircling relationship around the body part; and
    inflating means including a frangible member within said envelope for rapidly generating a supply of substantially only gas therein, said frangible member being accessible from the exterior of said envelope through the flexible walls thereof, whereby said frangible member may be manually ruptured to rapidly generate gas within said envelope, thereby causing said envelope to expand rapidly without further manipulation thereof and apply a compressive force to the body part.

2. A compression device according to claim 1 wherein said securing means comprises a sleeve adapted to encircle the body part with said envelope disposed between said body part and said sleeve.

3. A compression device according to claim 1 wherein said securing means comprises first and second mating fastening elements affixed to said envelope adjacent two opposite edges thereof.

4. A compression device according to claim 3 wherein said fastening elements comprise the mating elements of a separable fabric fastener.

5. A compression device according to claim 3 or 4 wherein said envelope completely encircles the body part with said opposite edges thereof in overlapping relationship.

6. A compression device according to claim 1 or 3 for applying a compressive force to a human arm and wrist, wherein said envelope has a hole therethrough for receipt of the thumb.

7. A compression device according to claim 1 further comprising a pressure release valve communicating with the interior of said envelope for releasing gas therefrom.

8. A compression device according to claim 1 wherein said frangible member is a capsule containing a plurality of chemical ingredients capable of generating gas when mixed, said frangible member having at least one thin frangible partition wall separating said chemical ingredients.

9. A compression device according to claim 1 wherein said frangible member is a capsule containing a first chemical ingredient and said envelope contains a second chemical ingredient, with said first and said second chemical ingredients capable of generating gas when mixed.

10. A compression device according to claim 8 wherein said expandable envelope contains a plurality of said capsules.

11. A compression device according to claim 8 or 9 wherein at least one of said chemical ingredients contains an antifreeze agent for preventing freezing thereof.

12. A compression device according to claim 2 wherein said sleeve and said envelope are made of flexible, transparent plastic sheet material.

13. A compression device according to claim 1 wherein said envelope is made of flexible, transparent plastic sheet material.

14. An anatomical compression device adapted to encircle and apply a compressive force to an anatomical body part, comprising:
   a completely sealed, flexible walled, expandible envelope having a central space adapted to receive the body part with the envelope encircling the body part; and
   inflating means including a frangible member within said envelope for rapidly generating a supply of substantially only gas therein, said frangible member being accessible from the exterior of said envelope through the flexible walls thereof, whereby said frangible member may be manually ruptured to rapidly generate gas within said envelope, thereby causing said envelope to expand rapidly without further manipulation thereof and apply a compressive force to the body part.

15. A compression device according to claim 14 wherein said frangible member is a capsule containing a plurality of chemical ingredients capable of generating gas when mixed, said frangible member having at least one thin frangible partition wall separating said chemical ingredients.

16. A compression device according to claim 14 wherein said frangible member is a capsule containing a first chemical ingredient and said envelope containing a second chemical ingredient, with said first and said second chemical ingredients capable of generating gas when mixed.

17. A compression device according to claim 14 wherein said expandible envelope contains a plurality of said capsules.

18. A compression device according to claim 15 or 16 wherein at least one of said chemical ingredients contains an antifreeze agent for preventing freezing thereof.

19. A compression device according to claim 14 wherein said envelope is made of flexible, transparent plastic sheet material.

20. A compression device according to claim 14 for applying a compressive force to a human arm and wrist, wherein said envelope has a hole therethrough for receipt of the thumb.

21. A compression device according to claim 14 further comprising a pressure release valve communicating with the interior of said envelope for releasing gas therefrom.

* * * * *